United States Patent
Fukuta et al.

(10) Patent No.: US 10,702,582 B2
(45) Date of Patent: Jul. 7, 2020

(54) HGF PREPARATION SUITABLE FOR TREATMENT OF NEUROLOGICAL DISORDERS

(71) Applicant: KRINGLE PHARMA INC., Osaka (JP)

(72) Inventors: Kazuhiro Fukuta, Osaka (JP); Hayao Inoue, Osaka (JP)

(73) Assignee: KRINGLE PHARMA INC., Osaka (JP)

(*) Notice: Subject to any disclaimer, the term of this patent is extended or adjusted under 35 U.S.C. 154(b) by 0 days.

(21) Appl. No.: 16/235,132

(22) Filed: Dec. 28, 2018

(65) Prior Publication Data

US 2019/0117732 A1    Apr. 25, 2019

Related U.S. Application Data

(62) Division of application No. 15/507,886, filed as application No. PCT/JP2015/074310 on Aug. 27, 2015, now Pat. No. 10,213,485.

(30) Foreign Application Priority Data

Sep. 10, 2014   (JP) .................................. 2014-184475

(51) Int. Cl.
| | |
|---|---|
| *A61K 38/18* | (2006.01) |
| *A61K 38/22* | (2006.01) |
| *A61K 47/02* | (2006.01) |
| *A61K 47/12* | (2006.01) |
| *A61K 47/26* | (2006.01) |
| *A61K 9/08* | (2006.01) |
| *A61K 9/19* | (2006.01) |
| *A61P 9/10* | (2006.01) |
| *A61P 25/16* | (2006.01) |
| *A61P 25/14* | (2006.01) |
| *A61P 25/28* | (2006.01) |
| *A61K 9/00* | (2006.01) |
| *A61K 47/18* | (2017.01) |

(52) U.S. Cl.
CPC ........ *A61K 38/1833* (2013.01); *A61K 9/0019* (2013.01); *A61K 9/0085* (2013.01); *A61K 9/08* (2013.01); *A61K 9/19* (2013.01); *A61K 38/22* (2013.01); *A61K 47/02* (2013.01); *A61K 47/12* (2013.01); *A61K 47/183* (2013.01); *A61K 47/26* (2013.01); *A61P 9/10* (2018.01); *A61P 25/14* (2018.01); *A61P 25/16* (2018.01); *A61P 25/28* (2018.01)

(58) Field of Classification Search
None
See application file for complete search history.

(56) References Cited

U.S. PATENT DOCUMENTS

| | | | |
|---|---|---|---|
| 5,587,359 A | 12/1996 | Higashio et al. | |
| 6,333,309 B1 | 12/2001 | Higashio et al. | |
| 6,699,837 B2 * | 3/2004 | Nakamura | A61K 38/1833 |
| | | | 514/17.7 |
| 7,550,565 B2 | 6/2009 | Nissen | |
| 8,518,880 B2 * | 8/2013 | Okano | A61K 9/0004 |
| | | | 514/17.7 |
| 8,575,099 B2 * | 11/2013 | Nakamura | C07K 14/4753 |
| | | | 424/450 |
| 8,927,493 B2 | 1/2015 | Tomita | |
| 9,872,899 B2 | 1/2018 | Tobin | |
| 9,873,734 B2 | 1/2018 | Fung | |
| 10,058,590 B2 * | 8/2018 | Nakamura | A61K 48/005 |
| 10,213,485 B2 * | 2/2019 | Fukuta | A61K 47/12 |
| 2003/0176347 A1 | 9/2003 | Nakamura et al. | |
| 2006/0229245 A1 * | 10/2006 | Tanaka | A61K 9/0019 |
| | | | 514/7.6 |
| 2007/0021335 A1 | 1/2007 | Takeo et al. | |
| 2009/0233863 A1 | 9/2009 | Adachi et al. | |
| 2012/0021040 A9 | 1/2012 | Okano et al. | |

FOREIGN PATENT DOCUMENTS

| | | |
|---|---|---|
| CN | 101785856 | 7/2010 |
| EP | 2 351 574 | 8/2011 |
| JP | 9-25241 | 1/1997 |
| JP | 2011-173916 | 9/2011 |
| WO | 90/10651 | 9/1990 |
| WO | 00/72873 | 12/2000 |
| WO | 02/22162 | 3/2002 |
| WO | 2005/034985 | 4/2005 |

(Continued)

OTHER PUBLICATIONS

Funakoshi et al., Current Signal Transduction Therapy, 6:156-167, 2011.*
Sun et al., The Journal of Neuroscience, 22(15):6537-6548, Aug. 1, 2002.*
Niimura et al., Neuroscience Letters, 407:136-140, 2006.*
Fukuta 1.132 Declaration submitted in U.S. Appl. No. 12/226,447, dated Apr. 26, 2013.*
Extended European Search Report dated Jun. 4, 2018 in corresponding European patent application No. 15840062.2.
Costantino et al., "Effect of Excipients on the Stability and Structure of Lyophilized Recombinant Human Growth Hormone", Journal of Pharmaceutical Sciences, vol. 87, No. 11, Nov. 1988, pp. 1412-1420.

(Continued)

*Primary Examiner* — Marianne P Allen
(74) *Attorney, Agent, or Firm* — Wenderoth, Lind & Ponack, L.L.P.

(57) ABSTRACT

The present invention provides a hepatocyte growth factor (HGF) preparation in the form of an injection or the like that is highly safe for central nerves and highly stable and can be used for intrathecal or intracerebroventricular administration or for administration into the spinal or cerebral parenchyma for the treatment of central nervous system diseases. The HGF preparation of the present invention contains an HGF protein as an active ingredient and lactose, glycine, sodium chloride, a pH buffering agent and a surfactant as additional ingredients.

9 Claims, No Drawings

Specification includes a Sequence Listing.

(56) References Cited

FOREIGN PATENT DOCUMENTS

| WO | 2007/122976 | 11/2007 |
|---|---|---|
| WO | 2008/102849 | 8/2008 |
| WO | 2008/105507 | 9/2008 |
| WO | 2014/089487 | 6/2014 |

OTHER PUBLICATIONS

Vemuri et al., "Effect of Cryoprotectants on Freezing, Lyophilization, and Storage of Lyophilized Recombinant Alpha 1-Antitrypsin Formulations", PDA Journal of Pharmaceutical Science and Techno., Parenteral Drug Association, vol. 48, No. 5, Sep.-Oct. 1994, pp. 241-246.

International Search Report dated Nov. 24, 2015 in International Application No. PCT/JP2015/074310.

Toshikazu Nakamura et al., "Partial Purification and Characterization of Hepatocyte Growth Factor From Serum of Hepatectomized Rats", Biochemical and Biophysical Research Communications, Aug. 16, 1984, vol. 122, No. 3, 1984, pp. 1450-1459.

Takahiro Nakamura et al., "Hepatocyte growth factor twenty years on: Much more than a growth factor", Journal of Gastroenterology and Hepatology 26 (2011), pp. 188-202.

Jeong Soo Park et al., "Overproduction of recombinant human hepatocyte growth factor in Chinese hamster ovary cells", Protein Expression and Purification, vol. 70, Issue 2, Apr. 2010, pp. 231-235, abstract only.

Flavio Maina et al., "Hepatocyte growth factor, a versatile signal for developing neurons", Nature Neuroscience, Mar. 1999, vol. 2, No. 3, pp. 213-217.

Hiroshi Funakoshi et al., "Hepatocyte Growth Factor (HGF): Neurotrophic Functions and Therapeutic Implications for Neuronal Injury/Diseases", Current Signal Transduction Therapy, 2011, vol. 6, pp. 156-167.

Shigeyuki Honda et al., "Localization and functional coupling of HGF and c-Met/HGF receptor in rat brain: implication as neurotrophic factor", Molecular Brain Research vol. 32 (1995) pp. 197-210.

Allen Ebens et al., "Hepatocyte Growth Factor/Scatter Factor Is an Axonal Chemoattractant and a Neurotrophic Factor for Spinal Motor Neurons", Neuron, vol. 17, pp. 1157-1172, Dec. 1996.

Aya Ishigaki et al., "Intrathecal Delivery of Hepatocyte Growth Factor From Amyotrophic Lateral Sclerosis Onset Suppresses Disease Progression in Rat Amyotrophic Lateral Sclerosis Model", J Neuropathol Exp Neurol, vol. 66, No. 11, Nov. 2007, pp. 1037-1044.

Kazuya Kitamura et al., "Human Hepatocyte Growth Factor Promotes Functional Recovery in Primates after Spinal Cord Injury", PLos One, vol. 6, Nov. 2011.

Tsutomu Arakawa, "Mechanism of stabilization of Proteins by Additives on Freezing", Protein, nucleic acid and enzyme, 1992, vol. 37, No. 9, pp. 1517 to 1523, partial English translation.

Japan Pharmaceutical Excipients Council, Lactose, Monohydrate, revised Handbook of Pharmaceutical Excipients, Yakuji Nippo Ltd., Feb. 28, 2007, pp. 650 to 658, partial English translation.

Yuta Kato et al., "A study on the Differences in Additives between Brand-Name and Generic Injection Drugs", Japanese Journal of Generic Medicines, 2013, vol. 7, No. 2, pp. 110 to 115, partial English translation.

International Preliminary Report on Patentability (Chapter I) dated Mar. 14, 2017 issued in International Patent Application No. PCT/JP2015/074310.

Explanation of Circumstances Concerning Accelerated Examination filed Oct. 13, 2017 in Japanese Application No. 2016-547358, with English translation.

* cited by examiner

SEQUENCE LISTING

```
<160> NUMBER OF SEQ ID NOS: 6

<210> SEQ ID NO 1
<211> LENGTH: 2187
<212> TYPE: DNA
<213> ORGANISM: Homo sapiens

<400> SEQUENCE: 1
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgtttttgat aaagcaagaa aacaatgcct ctggttcccc     300
ttcaatagca tgtcaagtgg agtgaaaaaa gaatttggcc atgaatttga cctctatgaa     360
```

```
aacaaagact acattagaaa ctgcatcatt ggtaaaggac gcagctacaa gggaacagta      420
tctatcacta agagtggcat caaatgtcag ccctggagtt ccatgatacc acacgaacac      480 agcttttgc cttcgagcta tcggggtaaa gacctacagg aaaactactg tcgaaatcct       540
cgaggggaag aaggggggacc ctggtgtttc acaagcaatc cagaggtacg ctacgaagtc     600
tgtgacattc ctcagtgttc agaagttgaa tgcatgacct gcaatgggga gagttatcga     660
ggtctcatgg atcatacaga atcaggcaag atttgtcagc gctgggatca tcagacacca     720
caccggcaca aattcttgcc tgaaagatat cccgacaagg gctttgatga taattattgc     780
cgcaatcccg atggccagcc gaggccatgg tgctatactc ttgaccctca cacccgctgg     840
gagtactgtg caattaaaac atgcgctgac aatactatga atgacactga tgttcctttg     900
gaaacaactg aatgcatcca aggtcaagga gaaggctaca gggcactgt caataccatt       960 tggaatggaa ttccatgtca gcgttgggat tctcagtatc ctcacgagca tgacatgact    1020
cctgaaaatt tcaagtgcaa ggacctacga gaaaattact gccgaaatcc agatgggtct    1080
gaatcaccct ggtgttttac cactgatcca acatccgag ttggctactg ctcccaaatt     1140
ccaaactgtg atatgtcaca tggacaagat tgttatcgtg ggaatggcaa aaattatatg    1200
ggcaacttat cccaaacaag atctggacta acatgttcaa tgtgggacaa gaacatggaa    1260
gacttacatc gtcatatctt ctgggaacca gatgcaagta agctgaatga gaattactgc    1320
cgaaatccag atgatgatgc tcatggaccc tggtgctaca cgggaaatcc actcattcct    1380
tgggattatt gccctatttc tcgttgtgaa ggtgatacca cacctacaat agtcaattta    1440
gaccatcccg taatatcttg tgccaaaacg aaacaattgc gagttgtaaa tgggattcca    1500
acacgaacaa acataggatg gatggttagt ttgagataca gaaataaaca tatctgcgga    1560
ggatcattga taaaggagag ttgggttctt actgcacgac agtgtttccc ttctcgagac    1620
ttgaaagatt atgaagcttg gcttggaatt catgatgtcc acggaagagg agatgagaaa    1680
tgcaaacagg ttctcaatgt ttcccagctg gtatatggcc ctgaaggatc agatctggtt    1740
ttaatgaagc ttgccaggcc tgctgtcctg gatgattttg ttagtacgat tgatttacct    1800
aattatggat gcacaattcc tgaaaagacc agttgcagtg tttatggctg gggctacact    1860
ggattgatca actatgatgg cctattacga gtggcacatc tctatataat gggaaatgag    1920
aaatgcagcc agcatcatcg agggaaggtg actctgaatg agtctgaaat atgtgctggg    1980
gctgaaaaga ttggatcagg accatgtgag ggggattatg gtggcccact tgtttgtgag    2040
caacataaaa tgagaatggt tcttggtgtc attgttcctg gtcgtggatg tgccattcca    2100
aatcgtcctg gtattttgt ccgagtagca tattatgcaa aatggataca caaaattatt     2160
ttaacatata aggtaccaca gtcatag                                         2187

<210> SEQ ID NO 2
<211> LENGTH: 2172
<212> TYPE: DNA
<213> ORGANISM: Homo sapiens

<400> SEQUENCE: 2
atgtgggtga ccaaactcct gccagccctg ctgctgcagc atgtcctcct gcatctcctc       60
ctgctcccca tcgccatccc ctatgcagag ggacaaagga aagaagaaa tacaattcat       120 gaattcaaaa aatcagcaaa gactacccta atcaaaatag atccagcact gaagataaaa      180
accaaaaaag tgaatactgc agaccaatgt gctaatagat gtactaggaa taaggacttg      240
```

| | | |
|---|---|---|
| ccattcactt gcaaggcttt tgttttttgat aaagcaagaa acaatgcct ctggttcccc | 300 | |
| ttcaatagca tgtcaagtgg agtgaaaaaa gaatttggcc atgaatttga cctctatgaa | 360 | |
| aacaaagact acattagaaa ctgcatcatt ggtaaaggac gcagctacaa gggaacagta | 420 | |
| tctatcacta agagtggcat caaatgtcag ccctggagtt ccatgatacc acacgaacac | 480 | |
| agctatcggg gtaaagacct acaggaaaac tactgtcgaa atcctcgagg ggaagaaggg | 540 | |
| ggaccctggt gtttcacaag caatccagag gtacgctacg aagtctgtga cattcctcag | 600 | |
| tgttcagaag ttgaatgcat gacctgcaat ggggagagtt atcgaggtct catggatcat | 660 | |
| acagaatcag gcaagatttg tcagcgctgg gatcatcaga caccacaccg gcacaaattc | 720 | |
| ttgcctgaaa gatatcccga caagggcttt gatgataatt attgccgcaa tcccgatggc | 780 | |
| cagccgaggc catggtgcta tactcttgac cctcacaccc gctgggagta ctgtgcaatt | 840 | |
| aaaacatgcg ctgacaatac tatgaatgac actgatgttc ctttggaaac aactgaatgc | 900 | |
| atccaaggtc aaggagaagg ctacagggggc actgtcaata ccatttggaa tggaattcca | 960 | |
| tgtcagcgtt gggattctca gtatcctcac gagcatgaca tgactcctga aaatttcaag | 1020 | |
| tgcaaggacc tacgagaaaa ttactgccga aatccagatg ggtctgaatc accctggtgt | 1080 | |
| tttaccactg atccaaacat ccgagttggc tactgctccc aaattccaaa ctgtgatatg | 1140 | |
| tcacatggac aagattgtta tcgtgggaat ggcaaaaatt atatgggcaa cttatcccaa | 1200 | |
| acaagatctg gactaacatg ttcaatgtgg acaagaaca tggaagactt acatcgtcat | 1260 | |
| atcttctggg aaccagatgc aagtaagctg aatgagaatt actgccgaaa tccagatgat | 1320 | |
| gatgctcatg gaccctggtg ctacacggga atccactca ttccttggga ttattgccct | 1380 | |
| atttctcgtt gtgaaggtga taccacacct acaatagtca atttagacca tcccgtaata | 1440 | |
| tcttgtgcca aaacgaaaca attgcgagtt gtaaatggga ttccaacacg aacaaacata | 1500 | |
| ggatggatgg ttagtttgag atacagaaat aaacatatct gcggaggatc attgataaag | 1560 | |
| gagagttggg ttcttactgc acgacagtgt ttcccttctc gagacttgaa agattatgaa | 1620 | |
| gcttggcttg gaattcatga tgtccacgga agaggagatg agaaatgcaa acaggttctc | 1680 | |
| aatgtttccc agctggtata tggccctgaa ggatcagatc tggttttaat gaagcttgcc | 1740 | |
| aggcctgctg tcctggatga ttttgttagt acgattgatt tacctaatta tggatgcaca | 1800 | |
| attcctgaaa agaccagttg cagtgtttat ggctggggct acactggatt gatcaactat | 1860 | |
| gatggcctat tacgagtggc acatctctat ataatgggaa atgagaaatg cagccagcat | 1920 | |
| catcgaggga aggtgactct gaatgagtct gaaatatgtg ctggggctga aaagattgga | 1980 | |
| tcaggaccat gtgaggggga ttatggtggc ccacttgttt gtgagcaaca taaaatgaga | 2040 | |
| atggttcttg gtgtcattgt tcctggtcgt ggatgtgcca ttccaaatcg tcctggtatt | 2100 | |
| tttgtccgag tagcatatta tgcaaaatgg atacacaaaa ttattttaac atataaggta | 2160 | |
| ccacagtcat ag | 2172 | |

<210> SEQ ID NO 3
<211> LENGTH: 728
<212> TYPE: PRT
<213> ORGANISM: Homo sapiens

<400> SEQUENCE: 3

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

```
Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
            130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
                435                 440                 445
```

-continued

```
Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 4
<211> LENGTH: 723
<212> TYPE: PRT
<213> ORGANISM: Homo sapiens

<400> SEQUENCE: 4

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95
```

```
Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
                180                 185                 190

Tyr Glu Val Cys Asp Ile Pro Gln Cys Ser Glu Val Glu Cys Met Thr
            195                 200                 205

Cys Asn Gly Glu Ser Tyr Arg Gly Leu Met Asp His Thr Glu Ser Gly
            210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
                260                 265                 270

Thr Arg Trp Glu Tyr Cys Ala Ile Lys Thr Cys Ala Asp Asn Thr Met
            275                 280                 285

Asn Asp Thr Asp Val Pro Leu Glu Thr Thr Glu Cys Ile Gln Gly Gln
            290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
            325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
            355                 360                 365

Val Gly Tyr Cys Ser Gln Ile Pro Asn Cys Asp Met Ser His Gly Gln
            370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Ala His Gly Pro Trp Cys Tyr
            435                 440                 445

Thr Gly Asn Pro Leu Ile Pro Trp Asp Tyr Cys Pro Ile Ser Arg Cys
            450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
            485                 490                 495

Arg Thr Asn Ile Gly Trp Met Val Ser Leu Arg Tyr Arg Asn Lys His
            500                 505                 510
```

-continued

```
Ile Cys Gly Gly Ser Leu Ile Lys Glu Ser Trp Val Leu Thr Ala Arg
515                 520                 525

Gln Cys Phe Pro Ser Arg Asp Leu Lys Asp Tyr Glu Ala Trp Leu Gly
    530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
            580                 585                 590

Asp Leu Pro Asn Tyr Gly Cys Thr Ile Pro Glu Lys Thr Ser Cys Ser
        595                 600                 605

Val Tyr Gly Trp Gly Tyr Thr Gly Leu Ile Asn Tyr Asp Gly Leu Leu
    610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655

Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 5
<211> LENGTH: 697
<212> TYPE: PRT
<213> ORGANISM: Homo sapiens

<400> SEQUENCE: 5

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
    130                 135                 140

Tyr Cys Arg Asn Pro Arg Gly Glu Glu Gly Gly Pro Trp Cys Phe Thr
145                 150                 155                 160
```

-continued

```
Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
            180                 185                 190

Asp His Thr Glu Ser Gly Lys Ile Cys Gln Arg Trp Asp His Gln Thr
        195                 200                 205

Pro His Arg His Lys Phe Leu Pro Glu Arg Tyr Pro Asp Lys Gly Phe
    210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
            260                 265                 270

Glu Cys Ile Gln Gly Gln Gly Glu Gly Tyr Arg Gly Thr Val Asn Thr
        275                 280                 285

Ile Trp Asn Gly Ile Pro Cys Gln Arg Trp Asp Ser Gln Tyr Pro His
    290                 295                 300

Glu His Asp Met Thr Pro Glu Asn Phe Lys Cys Lys Asp Leu Arg Glu
305                 310                 315                 320

Asn Tyr Cys Arg Asn Pro Asp Gly Ser Glu Ser Pro Trp Cys Phe Thr
                325                 330                 335

Thr Asp Pro Asn Ile Arg Val Gly Tyr Cys Ser Gln Ile Pro Asn Cys
            340                 345                 350

Asp Met Ser His Gly Gln Asp Cys Tyr Arg Gly Asn Gly Lys Asn Tyr
        355                 360                 365

Met Gly Asn Leu Ser Gln Thr Arg Ser Gly Leu Thr Cys Ser Met Trp
    370                 375                 380

Asp Lys Asn Met Glu Asp Leu His Arg His Ile Phe Trp Glu Pro Asp
385                 390                 395                 400

Ala Ser Lys Leu Asn Glu Asn Tyr Cys Arg Asn Pro Asp Asp Asp Ala
                405                 410                 415

His Gly Pro Trp Cys Tyr Thr Gly Asn Pro Leu Ile Pro Trp Asp Tyr
            420                 425                 430

Cys Pro Ile Ser Arg Cys Glu Gly Asp Thr Thr Pro Thr Ile Val Asn
        435                 440                 445

Leu Asp His Pro Val Ile Ser Cys Ala Lys Thr Lys Gln Leu Arg Val
    450                 455                 460

Val Asn Gly Ile Pro Thr Arg Thr Asn Ile Gly Trp Met Val Ser Leu
465                 470                 475                 480

Arg Tyr Arg Asn Lys His Ile Cys Gly Gly Ser Leu Ile Lys Glu Ser
                485                 490                 495

Trp Val Leu Thr Ala Arg Gln Cys Phe Pro Ser Arg Asp Leu Lys Asp
            500                 505                 510

Tyr Glu Ala Trp Leu Gly Ile His Asp Val His Gly Arg Gly Asp Glu
        515                 520                 525

Lys Cys Lys Gln Val Leu Asn Val Ser Gln Leu Val Tyr Gly Pro Glu
    530                 535                 540

Gly Ser Asp Leu Val Leu Met Lys Leu Ala Arg Pro Ala Val Leu Asp
545                 550                 555                 560

Asp Phe Val Ser Thr Ile Asp Leu Pro Asn Tyr Gly Cys Thr Ile Pro
                565                 570                 575

Glu Lys Thr Ser Cys Ser Val Tyr Gly Trp Gly Tyr Thr Gly Leu Ile
```

```
                    580              585              590
Asn Tyr Asp Gly Leu Leu Arg Val Ala His Leu Tyr Ile Met Gly Asn
                595              600              605

Glu Lys Cys Ser Gln His His Arg Gly Lys Val Thr Leu Asn Glu Ser
            610              615              620

Glu Ile Cys Ala Gly Ala Glu Lys Ile Gly Ser Gly Pro Cys Glu Gly
625              630              635              640

Asp Tyr Gly Gly Pro Leu Val Cys Glu Gln His Lys Met Arg Met Val
                645              650              655

Leu Gly Val Ile Val Pro Gly Arg Gly Cys Ala Ile Pro Asn Arg Pro
            660              665              670

Gly Ile Phe Val Arg Val Ala Tyr Tyr Ala Lys Trp Ile His Lys Ile
            675              680              685

Ile Leu Thr Tyr Lys Val Pro Gln Ser
            690              695
```

<210> SEQ ID NO 6
<211> LENGTH: 692
<212> TYPE: PRT
<213> ORGANISM: Homo sapiens

<400> SEQUENCE: 6

```
Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
                20                  25                  30

Val Asn Thr Ala Asp Gln Cys Ala Asn Arg Cys Thr Arg Asn Lys Gly
            35                  40                  45

Leu Pro Phe Thr Cys Lys Ala Phe Val Phe Asp Lys Ala Arg Lys Gln
50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Tyr Arg Gly Lys Asp Leu Gln Glu Asn Tyr Cys Arg Asn Pro
    130                 135                 140

Arg Gly Glu Glu Gly Gly Pro Trp Cys Phe Thr Ser Asn Pro Glu Val
145                 150                 155                 160

Arg Tyr Glu Val Cys Asp Ile Pro Gln Cys Ser Glu Val Glu Cys Met
                165                 170                 175

Thr Cys Asn Gly Glu Ser Tyr Arg Gly Leu Met Asp His Thr Glu Ser
            180                 185                 190

Gly Lys Ile Cys Gln Arg Trp Asp His Gln Thr Pro His Arg His Lys
        195                 200                 205

Phe Leu Pro Glu Arg Tyr Pro Asp Lys Gly Phe Asp Asp Asn Tyr Cys
    210                 215                 220

Arg Asn Pro Asp Gly Gln Pro Arg Pro Trp Cys Tyr Thr Leu Asp Pro
225                 230                 235                 240

His Thr Arg Trp Glu Tyr Cys Ala Ile Lys Thr Cys Ala Asp Asn Thr
                245                 250                 255
```

```
Met Asn Asp Thr Asp Val Pro Leu Glu Thr Thr Glu Cys Ile Gln Gly
                260                 265                 270

Gln Gly Glu Gly Tyr Arg Gly Thr Val Asn Thr Ile Trp Asn Gly Ile
            275                 280                 285

Pro Cys Gln Arg Trp Asp Ser Gln Tyr Pro His Glu His Asp Met Thr
        290                 295                 300

Pro Glu Asn Phe Lys Cys Lys Asp Leu Arg Glu Asn Tyr Cys Arg Asn
305                 310                 315                 320

Pro Asp Gly Ser Glu Ser Pro Trp Cys Phe Thr Thr Asp Pro Asn Ile
                325                 330                 335

Arg Val Gly Tyr Cys Ser Gln Ile Pro Asn Cys Asp Met Ser His Gly
            340                 345                 350

Gln Asp Cys Tyr Arg Gly Asn Gly Lys Asn Tyr Met Gly Asn Leu Ser
        355                 360                 365

Gln Thr Arg Ser Gly Leu Thr Cys Ser Met Trp Asp Lys Asn Met Glu
    370                 375                 380

Asp Leu His Arg His Ile Phe Trp Glu Pro Asp Ala Ser Lys Leu Asn
385                 390                 395                 400

Glu Asn Tyr Cys Arg Asn Pro Asp Asp Asp Ala His Gly Pro Trp Cys
                405                 410                 415

Tyr Thr Gly Asn Pro Leu Ile Pro Trp Asp Tyr Cys Pro Ile Ser Arg
            420                 425                 430

Cys Glu Gly Asp Thr Thr Pro Thr Ile Val Asn Leu Asp His Pro Val
        435                 440                 445

Ile Ser Cys Ala Lys Thr Lys Gln Leu Arg Val Val Asn Gly Ile Pro
450                 455                 460

Thr Arg Thr Asn Ile Gly Trp Met Val Ser Leu Arg Tyr Arg Asn Lys
465                 470                 475                 480

His Ile Cys Gly Gly Ser Leu Ile Lys Glu Ser Trp Val Leu Thr Ala
                485                 490                 495

Arg Gln Cys Phe Pro Ser Arg Asp Leu Lys Asp Tyr Glu Ala Trp Leu
            500                 505                 510

Gly Ile His Asp Val His Gly Arg Gly Asp Glu Lys Cys Lys Gln Val
        515                 520                 525

Leu Asn Val Ser Gln Leu Val Tyr Gly Pro Glu Gly Ser Asp Leu Val
    530                 535                 540

Leu Met Lys Leu Ala Arg Pro Ala Val Leu Asp Asp Phe Val Ser Thr
545                 550                 555                 560

Ile Asp Leu Pro Asn Tyr Gly Cys Thr Ile Pro Glu Lys Thr Ser Cys
                565                 570                 575

Ser Val Tyr Gly Trp Gly Tyr Thr Gly Leu Ile Asn Tyr Asp Gly Leu
            580                 585                 590

Leu Arg Val Ala His Leu Tyr Ile Met Gly Asn Glu Lys Cys Ser Gln
        595                 600                 605

His His Arg Gly Lys Val Thr Leu Asn Glu Ser Glu Ile Cys Ala Gly
    610                 615                 620

Ala Glu Lys Ile Gly Ser Gly Pro Cys Glu Gly Asp Tyr Gly Gly Pro
625                 630                 635                 640

Leu Val Cys Glu Gln His Lys Met Arg Met Val Leu Gly Val Ile Val
                645                 650                 655

Pro Gly Arg Gly Cys Ala Ile Pro Asn Arg Pro Gly Ile Phe Val Arg
            660                 665                 670

Val Ala Tyr Tyr Ala Lys Trp Ile His Lys Ile Ile Leu Thr Tyr Lys
```

```
            675                 680                 685

Val Pro Gln Ser
    690
```

HGF PREPARATION SUITABLE FOR TREATMENT OF NEUROLOGICAL DISORDERS

TECHNICAL FIELD

The present invention relates to a preparation containing a hepatocyte growth factor (hereinafter may be abbreviated as "HGF") protein. More particularly, the present invention relates to an HGF protein-containing preparation in the form of a lyophilized preparation, an injection or the like. The present invention also relates to an HGF protein-containing preparation in the form of a lyophilized preparation, an injection or the like, the preparation being suitable for the treatment of central nervous system diseases.

BACKGROUND ART

HGF was discovered as a biologically active protein having growth-promoting activity for mature hepatocytes (for example, see Non Patent Literature 1). Subsequent studies have revealed that HGF protein acts on not only hepatocytes but also various epithelial cells, vascular endothelial cells, etc., being involved in repair and regeneration of damaged tissues and organs (see Non Patent Literature 2). HGF protein can be mass-produced as a recombinant protein by bioengineering techniques (for example, see Non Patent Literature 3), and a recombinant HGF protein is expected to be used as a therapeutic agent not only for hepatitis and liver cirrhosis but also for nephropathy, wounds, etc. (see Non Patent Literature 2).

Furthermore, a large number of recent studies on gene expression analysis and gene functional analysis by knockout/knockin mouse approaches etc. have revealed that HGF protein also has the effect of promoting neuronal cell survival and neurite outgrowth and is an important neurotrophic factor (see Non Patent Literature 4 and 5).

HGF protein has neurotrophic activity on neuronal cells such as hippocampal neurons, dopaminergic neurons, cerebellar granule cells, sensory neurons and motor neurons (see Non Patent Literature 6). In particular, HGF protein has a strong effect of promoting the survival of motor neurons (see Non Patent Literature 7). This effect is comparable to that of glial cell line-derived neurotrophic factor (GDNF), a factor known to most strongly promote the survival of motor neurons.

Based on such neurotrophic activity, HGF protein has been reported to be applicable as a therapeutic agent for various neurological disorders including amyotrophic lateral sclerosis (ALS) and spinal cord injury (see Patent Literature 1 to 3 and Non Patent Literature 5, 8 and 9).

In general, protein pharmaceuticals are injected intravenously, subcutaneously or intramuscularly. However, proteins administered via such a route can very hardly transfer to central nervous system tissues across the blood-brain barrier between brain tissues and blood vessels, as is commonly known. Therefore, when HGF protein is used for the treatment of central nervous system diseases, intrathecal or intracerebroventricular administration, which allows direct delivery of HGF protein to central nervous system tissues, is considered to be effective instead of intravenous, subcutaneous or intramuscular injection, which is a route used for the treatment of common organ diseases (see Non Patent Literature 8 and 9). Intrathecal or intracerebroventricular administration is used also in the anticancer drug treatment of brain tumor. In addition, direct administration of HGF protein into the cerebral or spinal parenchyma is another possible administration route for the treatment of central nervous system diseases.

For the production of HGF protein pharmaceuticals, the development of stabilized HGF protein preparations is required. Patent Literature 4 discloses an HGF protein preparation which is an aqueous solution containing an HGF protein (also called TCF-II) plus a stabilizer such as albumin, human serum, gelatin, sorbitol, mannitol and xylitol (see Patent Literature 4). However, this aqueous HGF solution has some disadvantages. One is that the HGF aqueous solution gradually become turbid and gelatinized during storage due to aggregation of HGF protein molecules. Another is that the HGF aqueous solution is poor in physicochemical stability, for example, is prone to formation of HGF protein-based polymers (formation of HGF polymers), resulting in reduction in biological activity of HGF.

In order to provide a solution to prevent such polymer formation, for example, Patent literature 5 discloses a lyophilized HGF preparation containing HGF plus a stabilizer such as arginine, lysine, histidine, glutamine, proline, glutamic acid and aspartic acid (see Patent Literature 5). Patent Literature 6 discloses a lyophilized HGF preparation containing HGF plus a stabilizer such as glycine, alanine, sorbitol, mannitol and dextran sulfate (see Patent Literature 6). Patent Literature 7 discloses a lyophilized HGF preparation containing HGF plus purified sucrose, alanine and the like (see Patent Literature 7).

Injections prepared from these preparations are supposedly safe to use for intravenous, subcutaneous or intramuscular administration, which is a route used for the treatment of common organ diseases. However, for example in the case of intrathecal or intracerebroventricular administration, since HGF protein is directly delivered to the central nervous system, all the ingredients of the HGF preparation, including various additives, need to have been fully confirmed safe for the central nervous system. So far, there is no disclosure of HGF preparations publicly confirmed safe to use for intrathecal or intracerebroventricular administration or for administration into the spinal or cerebral parenchyma.

There is a need for highly safe HGF preparations that can be used for intrathecal or intracerebroventricular administration or for administration into the spinal or cerebral parenchyma for the treatment of central nervous system diseases.

CITATION LIST

Patent Literature

Patent Literature 1: WO 2002/22162 (US Pub. No. 2003/0176347)
Patent Literature 2: WO 2007/122976 (U.S. Pat. No. 8,575,099)
Patent Literature 3: WO 2008/105507 (U.S. Pat. No. 8,518,880)
Patent Literature 4: WO 90/10651 (EP Patent No. 0462277)
Patent Literature 5: WO 00/72873 (EP Patent No. 1180368)
Patent Literature 6: JP-A 9-25241 (U.S. Pat. No. 7,173,008)
Patent literature 7: WO 2008/102849 (U.S. Pat. No. 8,461,112)

Non Patent Literature

Non Patent Literature 1:
T. Nakamura et al., Biochem. Biophys. Res. Commun., vol. 122, p. 1450, 1984

Non Patent Literature 2:
T. Nakamura et al., J. Gastroenterol. Hepatol., vol. 26, Suppl. 1, pp. 188-202 (2011)
Non Patent Literature 3:
Jeong Soo Park et al., Protein Expr. Purif., vol. 70, p. 231-235 (2010)
Non Patent Literature 4:
Flavio Maina et al., Nat. Neurosci., vol. 2, pp. 213-217 (1999)
Non Patent Literature 5:
Funakoshi H et al., Current Signal Transduction Therapy vol. 6, pp. 156-167 (2011)
Non Patent Literature 6:
Honda, S. et al., Brain Res. Mol. Brain Res. vol. 32, pp. 197-210 (1995)
Non Patent Literature 7:
Allen Ebens et al., Neuron, vol. 17, pp. 1157-1172 (1996)
Non Patent Literature 8:
Ishigaki A et al., J Neuropathol Exp Neurol., vol. 66, pp. 1037-1044 (2007)
Non Patent Literature 9:
Kitamura K et al., PLoS One., vol. 6: e27706 (2011)

SUMMARY OF INVENTION

Technical Problem

An object of the present invention is to provide an HGF preparation in the form of an injection or the like that is highly safe for central nerves and can be used for intrathecal or intracerebroventricular administration or for administration into the spinal or cerebral parenchyma for the treatment of central nervous system diseases. In general, the HGF preparation is also required to be highly stable so that it can be practically used as a pharmaceutical product. Accordingly, another object of the present invention is to provide a highly stable HGF preparation in the form of an injection, a lyophilized preparation or the like.

Solution to Problem

The present inventors conducted intensive research to achieve the above-mentioned objects. As a result, the present inventors found that the formation of HGF protein-based polymers is prevented by addition of lactose, glycine, sodium chloride, a pH buffering agent and a surfactant to an HGF protein. The present inventors also found that an HGF solution containing these ingredients can be used as a stable HGF injection and that freeze-drying of the HGF solution yields a stable lyophilized HGF preparation. Moreover, it was found that an HGF injection containing the above ingredients is markedly less toxic to the central nervous system and highly safe for the nerve system such as central nerves.

Based on these findings, the present inventors conducted further research and completed the present invention. The HGF preparation of the present invention is stable enough to use as a pharmaceutical product. For example, the HGF injection of the present invention can be safely administered intrathecally or intracerebroventricularly or administered into the spinal or cerebral parenchyma for the treatment of various central nervous system diseases such as ALS and spinal cord injury.

That is, the present invention provides the following HGF preparation.
(1) A hepatocyte growth factor (HGF) preparation comprising an HGF protein as an active ingredient and lactose, glycine, sodium chloride, a pH buffering agent and a surfactant as additional ingredients.
(2) The HGF preparation according to the above (1), wherein the HGF preparation is a lyophilized preparation.
(3) The HGF preparation according to the above (2), wherein the HGF preparation is a lyophilized preparation obtained by freeze-drying of an aqueous solution comprising a hepatocyte growth factor (HGF) protein, lactose, glycine, sodium chloride, a pH buffering agent and a surfactant.
(4) The HGF preparation according to any one of the above (1) to (3), wherein the content of the lactose is in the range of 0.1 to 50 parts by weight relative to 1 part by weight of HGF.
(5) The HGF preparation according to the above (3), wherein the concentration of the lactose in the aqueous solution is in the range of 0.1 to 100 mg/mL.
(6) The HGF preparation according to the above (3), wherein the concentration of the glycine in the aqueous solution is in the range of 0.05 to 50 mg/mL.
(7) The HGF preparation according to the above (3), wherein the concentration of the HGF protein in the aqueous solution is in the range of 0.05 to 40 mg/mL.
(8) The HGF preparation according to the above (1), wherein the pH buffering agent is a combination of citric acid or a hydrate thereof with a salt of citric acid.
(9) The HGF preparation according to the above (1), wherein the surfactant is polysorbate.
(10) The HGF preparation according to the above (1), wherein the HGF preparation is an injection.
(11) The HGF preparation according to the above (10), wherein the injection is an aqueous solution obtained by dissolving the lyophilized preparation according to the above (2) in a pharmaceutically acceptable solvent.
(12) The HGF preparation according to the above (1), wherein the HGF preparation is for use in treatment of a central nervous system disease.
(13) The HGF preparation according to the above (12), wherein the central nervous system disease is amyotrophic lateral sclerosis (ALS), Alzheimer's disease, Parkinson's disease, Huntington's disease, spinocerebellar ataxia, spinal cord injury, cerebral infarction, cerebral ischemia or multiple sclerosis.
(14) The HGF preparation according to the above (1), wherein the HGF preparation is administered intrathecally or intracerebroventricularly or administered into spinal or cerebral parenchyma.
(15) The HGF preparation according to the above (10), wherein the concentration of the lactose in the injection is in the range of 0.1 to 100 mg/mL.
(16) The HGF preparation according to the above (10), wherein the concentration of the glycine in the injection is in the range of 0.05 to 50 mg/mL.
(17) The HGF preparation according to the above (10), wherein the concentration of the HGF protein in the injection is in the range of 0.05 to 40 mg/mL.
(18) The HGF preparation according to the above (1), wherein the HGF protein is a human HGF protein.
(19) The HGF preparation according to the above (18), wherein the HGF protein is a protein consisting of an amino acid sequence represented by SEQ ID NO: 5 or SEQ ID NO: 6.
(20) The HGF preparation according to the above (1), wherein the HGF protein is a protein which has 80% or more sequence identity with an amino acid sequence represented by SEQ ID NO: 5 and has a biological activity of HGF.

The present invention also relates to a method for stabilizing HGF, more particularly preventing formation of HGF protein-based polymers in an aqueous HGF solution or a lyophilized HGF preparation, and the method comprises using lactose, glycine, sodium chloride, a pH buffering agent and a surfactant.

Furthermore, the present invention relates to a method for treating a central nervous system disease, the method comprising administering the HGF preparation according to the above (1) intrathecally or intracerebroventricularly or administering the same into the spinal or cerebral parenchyma to a patient with a central nervous system disease.

Advantageous Effects of Invention

The HGF preparation of the present invention is a stable preparation and can be used safely for central nerves. Since the HGF injection of the present invention is highly safe for the central nervous system, for example, it can be administered intrathecally or intracerebroventricularly or administered into the spinal or cerebral parenchyma for the treatment of various central nervous system diseases such as ALS and spinal cord injury.

DESCRIPTION OF EMBODIMENTS

The HGF preparation of the present invention contains an HGF protein as an active ingredient and lactose, glycine, sodium chloride, a pH buffering agent and a surfactant as additional ingredients.

The HGF preparation of the present invention may further contain one or more additional active ingredients (medicinal ingredients) in addition to the HGF protein, but preferably contain no active ingredient except the HGF protein.

The dosage form of the HGF preparation of the present invention is not particularly limited, but preferred is, for example, a parenteral dosage form such as a lyophilized preparation and an injection. The lyophilized preparation is preferably a lyophilized preparation for injection.

The injection means a liquid composition which is injectable directly into the living body. In the case where the HGF preparation of the present invention is an injection, it may be abbreviated simply as an "HGF injection".

The lyophilized preparation means a preparation in which the ingredients are in a freeze-dried solid state. In the case where the HGF preparation of the present invention is a lyophilized preparation, it may be abbreviated simply as a "lyophilized HGF preparation". Typically, a lyophilized preparation is dissolved in an appropriate solvent (dissolving liquid) before use, and the solution is administered as an injection as it is or if needed after dilution in an appropriate solvent or the like. That is, it can be said that a solution obtained by dissolving a lyophilized preparation in a solvent is substantially equivalent to an injection.

The HGF preparation of the present invention is preferably a lyophilized preparation containing an HGF protein as an active ingredient and lactose, glycine, sodium chloride, a pH buffering agent and a surfactant as additional ingredients. Another preferable embodiment of the HGF preparation of the present invention is an HGF injection containing an HGF protein as an active ingredient and lactose, glycine, sodium chloride, a pH buffering agent and a surfactant as additional ingredients.

The HGF preparation of the present invention is highly safe for the central nervous system. The HGF preparation of the present invention including the HGF injection is so markedly less toxic to the central nervous system that it can be administered, for example, intrathecally or intracerebroventricularly or administered into the spinal or cerebral parenchyma. Therefore, the HGF preparation of the present invention is suitable for use in the treatment of various central nervous system diseases, etc.

The HGF protein in the present invention may be from any species without particular limitation, and HGF proteins from various animals (native HGF proteins or recombinant proteins produced by genetic engineering techniques) etc. can preferably be used. In the present invention, it is preferred to use, for example, an HGF protein from an animal for which the HGF preparation of the present invention is intended to be used. For example, when the HGF preparation of the present invention is intended to be used for humans, an HGF protein from humans (hereinafter may be referred to as a human HGF protein) is suitable as the HGF protein used in the present invention. More preferred is a recombinant human HGF protein. When the HGF preparation of the present invention is intended to be used for non-human mammals, HGFs from such animals are preferably used, and for example, HGF proteins from monkeys, cattle, horses, pigs, sheep, dogs, cats, rats, mice, rabbits, hamsters, guinea pigs, chimpanzees, etc. are usable. In addition, the HGF protein used in the present invention may be a 5-amino-acid-deleted-type HGF protein (dHGF).

The human HGF protein is preferably a protein encoded by a DNA consisting of the nucleotide sequence represented by SEQ ID NO: 1 or SEQ ID NO: 2, for example. More specifically, preferred are a protein consisting of the amino acid sequence represented by SEQ ID NO: 3, a protein consisting of the amino acid sequence represented by SEQ ID NO: 4, a protein consisting of the amino acid sequence represented by SEQ ID NO: 5, a protein consisting of the amino acid sequence represented by SEQ ID NO: 6, etc. In particular, the human HGF protein is preferably a protein having the amino acid sequence represented by SEQ ID NO: 5 or SEQ ID NO: 6, and more preferably a protein consisting of the amino acid sequence represented by SEQ ID NO: 5 or SEQ ID NO: 6. For example, the HGF protein consisting of the amino acid sequence represented by SEQ ID NO: 6 is a 5-amino-acid-deleted-type HGF protein (dHGF) in which 5 amino acid residues at positions 131 to 135 of the amino acid sequence represented by SEQ ID NO: 5 are deleted. The protein having the amino acid sequence represented by SEQ ID NO: 5 or SEQ ID NO: 6 is a naturally-occurring HGF protein (native HGF protein) in the human body and has activities of HGF, such as mitogenic activity and motogenic activity.

The HGF protein used in the present invention encompasses proteins which have at least about 80% or more, preferably about 90% or more, more preferably about 95% or more sequence identity with the amino acid sequence of HGF proteins (native HGF proteins) from various animals and have biological activities (mitogenic activity and motogenic activity) of HGF. The term "sequence identity" as used herein in connection with the amino acid sequence means the identity of amino acid residues between the amino acid sequences (primary structures) of two proteins. A number together with "% or more" represents the degree of the sequence identity.

The mitogenic and motogenic activities of the HGF protein can be confirmed, for example, according to the method described in J. Biol. Chem. 273, 22913-22920, 1998. Preferably, the HGF protein used for the present invention has mitogenic and motogenic activities as measured according to J. Biol. Chem. 273, 22913-22920, 1998 as high as usually about 50% or more, preferably about 70% or more, more preferably about 80% or more, still more preferably about 90% or more of those of the native HGF protein.

Examples of proteins which have the above-described sequence identity with native HGF proteins include proteins which have the same amino acid sequence as that represented by SEQ ID NO: 5 or 6 except for substitution, deletion and/or insertion of one to several amino acid residues or modification of one to several amino acid residues and have biological activities of HGF.

The term "several" generally means an integral number of 1 to 8 (1, 2, 3, 4, 5, 6, 7 and 8), and is usually 8, preferably 6, more preferably 5, still more preferably 3, particularly preferably 2. The amino acid to be inserted or substituted for the original one is preferably a natural amino acid, but may be an unnatural amino acid other than 20 kinds of gene-encoded amino acids. The unnatural amino acid may be any compound that has an amino group and a carboxyl group, and for example is γ-aminobutyric acid or the like.

The substitution of an amino acid residue means replacement of one amino acid residue with another in a polypeptide, and is preferably conservative substitution. The term "conservative substitution" means replacement of one to several amino acid residues with another (or other) chemically similar amino acid residue(s) without substantial change in the activity of the polypeptide. Examples of conservative substitution include a case where a hydrophobic amino acid residue is replaced by another hydrophobic amino acid residue, or a case where a polar amino acid residue is replaced with another polar amino acid residue with the same charge. The functionally similar amino acid(s) for conservative substitution of each amino acid is/are known in the art. Exemplary amino acids with a nonpolar (hydrophobic) side chain include glycine, alanine, valine, isoleucine, leucine, proline, tryptophan, phenylalanine and methionine. Exemplary neutral amino acids with a polar side chain include serine, threonine, tyrosine, glutamine, asparagine and cysteine. Exemplary positively-charged (basic) amino acids include arginine, histidine and lysine. Exemplary negatively-charged (acidic) amino acids include aspartic acid and glutamic acid.

The HGF protein contained in the preparation of the present invention may be of one kind, or a combination of two or more of the above-described ones.

The HGF protein used in the preparation of the present invention can be prepared by various methods as long as the purity of the prepared HGF protein is suitable for pharmaceutical use. Various preparation methods are known, and for example, the HGF protein can be obtained by extraction and purification from organs such as liver, spleen, lung, bone marrow, brain, kidney and placenta, blood cells such as platelets and leukocytes, plasma, serum and the like of mammals such as rats, cattle, horses and sheep.

A specific procedure of the extraction and purification of the HGF protein from the above living tissues etc. is, for example, as follows. Carbon tetrachloride is intraperitoneally injected to rats to induce hepatitis, the liver is isolated and homogenized, and the HGF protein is purified by ordinary protein purification methods such as column chromatography with S-sepharose, heparin sepharose, etc. and HPLC.

Alternatively, the HGF protein can be obtained by isolation and purification from the culture (culture supernatant, cultured cells, etc.) of primary cultured cells or established cell lines which produce the HGF protein. Alternatively, genetic engineering techniques can be used for the preparation of the HGF protein. Specifically, a gene encoding the HGF protein (preferably, a DNA consisting of the nucleotide sequence represented by SEQ ID NO: 1 or 2) is inserted into an appropriate vector, the vector is introduced into an appropriate host for transformation, and a recombinant HGF protein of interest is harvested from the culture of the resulting transformant (for example, see Biochem. Biophys. Res. Commun. 180: 1151-1158, 1991; J. Clin. Invest. 87: 1853-1857, 1991; Protein Expr. Purif. 70: 231-235, 2010; etc.). The host cell is not particularly limited, and various kinds of host cells conventionally used in genetic engineering techniques can be used. For example, *E. coli, Bacillus subtilis*, yeasts, filamentous fungi, plant cells, animal cells, etc. can be used. In an example where animal cells are used as the host cell, Chinese hamster ovary (CHO) cells, mouse C127 cells, monkey COS cells or other animal cells are transformed with an expression vector prepared by insertion of a cDNA encoding the amino acid sequence of a human HGF protein, the culture supernatant is separated, and the HGF protein in the supernatant is purified by, for example, column chromatography as exemplified above.

As long as the thus-obtained HGF protein has biological activities of HGF, it may be different from the native HGF protein in that the amino acid sequence has substitution, deletion and/or insertion of one or more amino acids. In this context, "one or more" is, for example, one to several (the term "several" is as defined above, and is for example 1 to 8, preferably 1 to 6, more preferably 1 to 5, still more preferably 1 to 3, particularly preferably 1 or 2; the same will apply hereinafter). The substitution is preferably conservative substitution. The HGF protein may be modified by substitution, deletion or insertion of a sugar chain(s). The "deletion, substitution and/or insertion of one or more amino acids" as used herein in connection with the amino acid sequence means deletion, substitution and/or insertion of a certain number of amino acids, which number substantially corresponds to the number of amino acids that can be deleted, substituted and/or inserted by well-known technical methods such as gene engineering and site-directed mutagenesis or in a naturally-occurring manner (generally one to several amino acids). The "HGF protein modified by substitution, deletion or insertion of a sugar chain(s)" means an HGF protein obtained by removing a sugar chain(s) from a native HGF protein by treatment with an enzyme or the like; an HGF protein obtained by mutating a glycosylation site(s) in the amino acid sequence of a native HGF protein so as not to allow glycosylation; an HGF protein obtained by mutating the amino acid sequence of a native HGF protein so as to allow glycosylation of a site(s) other than the natural glycosylation site(s); or the like.

The lactose, glycine, sodium chloride, pH buffering agent and surfactant used in the HGF preparation of the present invention are preferably the same as described in the pharmacopoeias of various countries (for example, the Japanese Pharmacopoeia, the United States Pharmacopeia, the European Pharmacopoeia, etc.). In the case where those not described in the pharmacopoeias are used, pharmaceutically acceptable ones are preferably used. The term "pharmaceutically acceptable" means being usually safe, less toxic, free from biological and other problems, and useful for preparing pharmaceutical preparations acceptable for animal or human use.

The lactose used in the HGF preparation of the present invention is preferably the same as described in the pharmacopoeias of various countries (for example, the Japanese Pharmacopoeia, the United States Pharmacopeia, the European Pharmacopoeia, etc.). The amount of the lactose is preferably about 0.1 to 50 parts by weight, more preferably about 0.5 to 10 parts by weight and still more preferably about 1 to 5 parts by weight (including 1 to 2 parts by weight, 1 to 3 parts by weight, 1 to 4 parts by weight, 1 to 5 parts by weight, 2 to 3 parts by weight, 2 to 4 parts by weight, 2 to 5 parts by weight, 3 to 4 parts by weight, 3 to 5 parts by weight and 4 to 5 parts by weight) relative to 1 part by weight of the HGF protein.

The glycine used in the HGF preparation of the present invention is preferably the same as described in the pharmacopoeias of various countries (for example, the Japanese Pharmacopoeia, etc.). The amount of the glycine is preferably about 0.01 to 1 part by weight, more preferably about 0.05 to 1 part by weight and still more preferably about 0.1 to 0.5 part by weight (including 0.1 to 0.2 part by weight, 0.1 to 0.3 part by weight, 0.1 to 0.4 part by weight, 0.1 to 0.5 part by weight, 0.2 to 0.3 part by weight, 0.2 to 0.4 part by weight, 0.2 to 0.5 part by weight, 0.3 to 0.4 part by weight, 0.3 to 0.5 part by weight and 0.4 to 0.5 part by weight) relative to 1 part by weight of the HGF protein.

The pH buffering agent used in the HGF preparation of the present invention means an agent which, once dissolved in a solvent such as water, can serve as a buffer, which has the effect of keeping the pH of the solution within a certain range. A typical example is a combination of a weak acid and a salt thereof. Preferable examples of the pH buffering agent include a combination of phosphoric acid, citric acid or boric acid with the corresponding salt, which can serve as phosphate buffer, citrate buffer or borate buffer once dissolved. More preferred is a combination of citric acid and a salt thereof, which can serve as citrate buffer. These weak acids and their salts may be in the form of a solvate, and the solvate is preferably a hydrate, for example. A solution of the pH buffering agent can serve as a buffer, which has the effects of adjusting the pH of an aqueous HGF solution and maintaining the solubility and stability of the HGF protein. Examples of the aqueous HGF solution in the present invention include an HGF injection; an aqueous solution prepared before a freeze-drying step in the course of the production of the lyophilized preparation described later; and an aqueous solution obtained by redissolving the lyophilized preparation in a solvent. When the HGF preparation is, for example, a lyophilized preparation, the pH buffering agent preferably has the effect of keeping the pH of an aqueous solution obtained by redissolving the HGF preparation within the range of about 4.5 to 8.0. When the HGF preparation is an HGF injection, the pH buffering agent preferably has the effect of keeping the pH of the injection within the range of about 4.5 to 8.0. Specifically, regardless of the form of the HGF preparations including an HGF injection and a lyophilized HGF preparation, the pH buffering agent in the present invention is preferably a combination of citric acid or its solvate with a citric acid salt or its solvate; more preferably a combination of citric acid or its hydrate with a citric acid salt; and still more preferably a combination of a citric acid hydrate with sodium citrate (preferably trisodium citrate dihydrate or trisodium citrate (anhydrous)). Citrate buffer is highly effective for stabilizing the HGF protein in an aqueous HGF solution and can contribute to the stabilization of the HGF protein in the HGF injection; the aqueous HGF solution prepared in the course of the production of the lyophilized HGF preparation; and the aqueous solution obtained by redissolving the lyophilized HGF preparation in a solvent. In a preferable embodiment, the amount of the pH buffering agent, for example, in the HGF injection, is such an amount as to give a concentration of preferably about 1 to 100 mM, more preferably about 1 to 20 mM in the injection. In a preferable embodiment, the amount of the pH buffering agent in the lyophilized preparation is such an amount as to give a concentration of preferably about 1 to 100 mM, more preferably about 1 to 20 mM in an aqueous solution before a freeze-drying step in the course of the production of the lyophilized preparation described later.

Examples of the surfactant used in the HGF preparation of the present invention include polysorbate (for example, polysorbate 20 (polyoxyethylene sorbitan monolaurate), polysorbate 80 (polyoxyethylene sorbitan monooleate), etc.), Pluronic (registered trademark) F-68 (GIBCO) and polyethylene glycol. Two or more of them may be used in combination. Preferred is polysorbate, and particularly preferred is polysorbate 80. The HGF protein easily adsorbs to the surface of a container of glass, resin or other materials, but the addition of such a surfactant can prevent the adsorption of the HGF protein to the container in the course of the production of the HGF preparation. The addition of the surfactant can also prevent the adsorption of the HGF protein to a container holding the HGF injection or the aqueous HGF solution obtained by redissolving the HGF preparation in a solvent. The amount of the surfactant in the HGF injection is, for example, such an amount as to give a concentration of preferably about 0.001 to 2.0% by weight, more preferably about 0.005 to 1.0% by weight in the injection. The amount of the surfactant in the lyophilized preparation is, for example, such an amount as to give a concentration of preferably about 0.001 to 2.0% by weight, more preferably about 0.005 to 1.0% by weight in an aqueous solution before a freeze-drying step in the course of the production of the lyophilized preparation described later.

The sodium chloride used in the HGF preparation of the present invention has the effect of maintaining the solubility of the HGF protein. That is, the addition of sodium chloride, particularly at about 150 mM or higher, increases the solubility of the HGF protein. In addition, the addition of sodium chloride can make the osmotic pressure of an aqueous HGF solution close to the osmotic pressure of the body fluid. The amount of the sodium chloride can be adjusted as appropriate according to the desired osmotic pressure ratio. Preferably, the amount of the sodium chloride is such an amount as to give an osmotic pressure ratio (relative to physiological saline (osmotic pressure ratio: 1)) of about 1 to 3, which is a range acceptable for injections for clinical use or animal use. The amount of the sodium chloride, for example, in the HGF injection, is such an amount as to give a concentration of preferably about 150 to 1000 mM, more preferably about 150 to 300 mM in the injection. The amount of the sodium chloride in the lyophilized preparation is, for example, such an amount as to give a concentration of preferably about 150 to 1000 mM, more preferably about 150 to 300 mM in an aqueous HGF solution prepared in the course of the production of the lyophilized preparation described later.

The production method of the HGF preparation of the present invention is not particularly limited. For example, the HGF preparation in the form of a lyophilized preparation can be produced by freeze-drying of an aqueous solution containing an HGF protein, lactose, glycine, sodium chloride, a pH buffering agent and a surfactant. The thus-obtained lyophilized preparation is a preferable embodiment of the HGF preparation of the present invention. For preparation of the aqueous solution used in the production of the lyophilized preparation, any method may be used without particular limitation as long as the aqueous solution contains an HGF protein, lactose, glycine, sodium chloride, a pH buffering agent and a surfactant. For example, to a solution of a purified HGF protein (typically containing a pH buffer, sodium chloride and a surfactant), lactose and glycine, and if needed, a pharmaceutically acceptable solvent (for example, sterilized water, distilled water for injection, purified water, buffer, physiological saline, etc.) are added to prepare the aqueous solution. In a preferable embodiment, the concentration of the HGF protein is adjusted to preferably about 0.05 to 40 mg/mL, more preferably about 0.1 to 40 mg/mL, and still more preferably about 0.1 to 20 mg/mL in the aqueous solution. The lactose is added in such an amount as to give a concentration of preferably about 0.1 to 100 mg/mL, more preferably about 0.5 to 50 mg/mL, and still more preferably about 1 to 20 mg/mL in the aqueous solution. The glycine is added in such an amount as to give a concentration of preferably about 0.05 to 50 mg/mL, more preferably about 0.05 to 20 mg/mL, and still more preferably about 0.1 to 10 mg/mL in the aqueous solution. This aqueous HGF solution can further contain one or more additional ingredients such as solubilizers, antioxidants, soothing agents and tonicity agents, if needed. In a preferable embodiment, the aqueous HGF solution is sterilized by filtration with a filter or the like, distributed into vials or ampules and then freeze-dried. The filter is preferably a sterilizing filter with a pore size of about 0.22 μm or less, for example. Preferable examples of the sterilizing filter include Durapore (registered trademark, manufactured by Merck) and Sartopore 2 (registered trademark, manufactured by Sartorius).

The method for freeze-drying of the aqueous solution is not particularly limited and ordinary freeze-drying methods can be used. An exemplary freeze-drying method comprises the following three steps: a freezing step in which cooling and freezing is performed under normal pressure; a primary drying step in which solute-free water is sublimed off under vacuum; and a secondary drying step in which water bound to solutes, such as adsorbed water and crystallization water, is removed. The freezing temperature of the freezing step is preferably about −60° C. to −40° C., the temperature of the primary drying step is preferably about −50° C. to 0° C., and the temperature of the secondary drying step is preferably about 4° C. to 40° C. The vacuum pressure is preferably about 0.1 to 1.5 Pa, and particularly preferably about 0.5 to 1.2 Pa. The pressure of the drying chamber is made to recover after the completion of freeze-drying. In a preferable method for pressure recovery, sterile air or inert gas (for example, sterile nitrogen gas, sterile helium gas, etc.) is fed into the chamber to allow the pressure to recover firstly to a level of about 70 to 100 kPa, more preferably about 80 to 95 kPa (primary pressure recovery) and then to atmospheric pressure (secondary pressure recovery). The vials are preferably plugged with stoppers after the primary pressure recovery, and the plugged vials are preferably sealed with caps immediately after the secondary pressure recovery. The ampules are preferably melt-sealed by applying heat to their tips (typically using a gas burner) after the completion of drying.

The lyophilized HGF preparation preferably has a moisture content of about 2% by weight or less.

The lyophilized HGF preparation of the present invention is less prone to formation of HGF protein-based polymers during storage and is highly stable. The term "protein-based polymer" means a substance in which plural protein monomers are bound together for example in a chain or net-like structure. In the present invention, a dimer, a trimer and a tetramer of HGF proteins are included.

Typically, the lyophilized HGF preparation of the present invention is dissolved in a pharmaceutically acceptable solvent and used in the form of an aqueous solution. The term "pharmaceutically acceptable" is as defined above. Preferable examples of the pharmaceutically acceptable solvent include distilled water for injection, physiological saline, various kinds of infusion (for example, 5% glucose solution, Ringer's solution, etc.) and artificial spinal fluid. The solvent is more preferably distilled water for injection or physiological saline. In a preferable embodiment, the lyophilized HGF preparation of the present invention is dissolved in a pharmaceutically acceptable solvent, such as distilled water for injection, to prepare a solution containing an HGF protein at a concentration of preferably about 0.05 to 40 mg/mL, more preferably about 0.1 to 40 mg/mL, still more preferably about 0.1 to 20 mg/mL, which solution can preferably be used as an injection.

The lyophilized HGF preparation of the present invention can be packed together with the above-described pharmaceutically acceptable solvent and provided as a kit.

The HGF injection of the present invention is preferably an aqueous solution containing an HGF protein, lactose, glycine, sodium chloride, a pH buffering agent and a surfactant. The lactose, the glycine, the sodium chloride, the pH buffering agent and the surfactant, and their preferable embodiments and the like are as described above.

The production method of the HGF injection of the present invention is not particularly limited. For example, the lyophilized HGF preparation is dissolved in a pharmaceutically acceptable solvent to prepare the HGF injection. Preferable examples of the pharmaceutically acceptable solvent include distilled water for injection, physiological saline, various kinds of infusion (for example, 5% glucose solution, Ringer's solution, etc.) and artificial spinal fluid. The solvent is more preferably distilled water for injection or physiological saline. Alternatively, the HGF injection of the present invention can be prepared by adding lactose and glycine, and if needed, a pharmaceutically acceptable solvent (for example, sterilized water, distilled water for injection, purified water, buffer, physiological saline, etc.) to an about 0.1 to 40 mg/mL aqueous solution of a purified HGF protein (typically containing a pH buffer, sodium chloride and a surfactant). For example, the aqueous solution used in the production of the lyophilized preparation described above, which solution contains an HGF protein, lactose, glycine, sodium chloride, a pH buffering agent and a surfactant, can be used as the HGF injection.

The concentration of the HGF protein in the HGF injection of the present invention is preferably about 0.05 to 40 mg/mL, more preferably about 0.1 to 40 mg/mL, and still more preferably about 0.1 to 20 mg/mL.

The concentration of the lactose in the HGF injection of the present invention is preferably about 0.1 to 100 mg/mL, more preferably about 0.5 to 50 mg/mL, and still more preferably about 1 to 20 mg/mL.

The concentration of the glycine in the HGF injection of the present invention is preferably about 0.05 to 50 mg/mL, more preferably about 0.05 to 20 mg/mL, and still more preferably about 0.1 to 10 mg/mL.

The pH of the HGF injection of the present invention is preferably about 4.5 to 8.0.

The HGF injection of the present invention can further contain one or more additional ingredients such as solubilizers, antioxidants, soothing agents and tonicity agents, if needed.

The HGF injection of the present invention is usually a clear solution. The HGF injection of the present invention is less prone to formation of HGF polymers during storage and is highly stable although it is in the state of a solution.

The intended use of the HGF preparation of the present invention is not particularly limited, but preferably, the HGF preparation is used as a pharmaceutical composition for the treatment or prevention of central nervous system diseases, for example, amyotrophic lateral sclerosis (ALS), Alzheimer's disease, Parkinson's disease, Huntington's disease, spinocerebellar ataxia, spinal cord injury, cerebral infarction, cerebral ischemia, multiple sclerosis, etc. In particular, the HGF preparation of the present invention is suitable for use in the treatment of central nervous system diseases.

The HGF preparation of the present invention including the HGF injection and the lyophilized HGF preparation can be administered, for example, intracerebroventricularly or intrathecally. For example, the HGF injection of the present invention is suitable as a preparation for intracerebroventricular or intrathecal administration. The intrathecal space, into which the HGF injection of the present invention is delivered in the case of intrathecal administration, is a space which is located around the spinal cord and filled with cerebrospinal fluid. This space is surrounded by a double-layer membrane consisting of arachnoid mater and dura mater. The intrathecal space is a space beneath the arachnoid mater, the inner layer of the double-layer membrane, and therefore, intrathecal administration means administration into the subarachnoid space. The space around the brain and the space around the spinal cord are both filled with cerebrospinal fluid, and the cerebral ventricles in the brain are also filled with cerebrospinal fluid. The cerebral ventricles, the pericerebral space and the intrathecal space are connected to form one continuous space, in which the cerebrospinal fluid circulates. Therefore, intracerebroventricular administration and intrathecal administration are both administration of a drug into the cerebrospinal fluid. Usually, intracerebroventricular administration and intrathecal administration are the substantially same administration route. In addition, the HGF preparation of the present invention including the HGF injection can be administered into the cerebral or spinal parenchyma. For intracerebroventricular or intrathecal administration or administration into the cerebral or spinal parenchyma, the injection may be administered as a bolus or continuously administered as an infusion using a syringe pump etc.

The intended use of the HGF preparation of the present invention is not limited only to the treatment of central nervous system diseases. Since the HGF preparation of the present invention has a sufficient stability for pharmaceutical use and is highly safe, it can be used for the treatment of diseases other than central nervous system diseases as well. In this case, an administration route suitable for the treatment of the target disease can be selected, and for example, intravenous injection, subcutaneous injection, intramuscular injection, local administration, etc. can be used.

The dose of the HGF preparation of the present invention can be determined as appropriate according to the kind of the target disease, the disease condition, etc. For example, in the case where the HGF injection is used for the treatment of central nervous system diseases, the daily dose of the HGF protein is preferably about 0.01 to 50 mg, and more preferably about 0.1 to 10 mg per adult. In this case, the HGF injection is preferably administered intracerebroventricularly or intrathecally. In addition, the HGF preparation of the present invention including the HGF injection may be diluted as appropriate with an appropriate pharmaceutically acceptable solvent before administration. Examples of the pharmaceutically acceptable solvent include distilled water for injection, physiological saline, various kinds of infusion (for example, 5% glucose solution, Ringer's solution, etc.) and artificial spinal fluid. More preferred are distilled water for injection and physiological saline.

The present invention also includes a method for treating a central nervous system disease, comprising administering, to a patient with a central nervous system disease, an HGF preparation containing an HGF protein as an active ingredient and lactose, glycine, sodium chloride, a pH buffering agent and a surfactant as additional ingredients.

The present invention also includes an HGF preparation containing an HGF protein as an active ingredient and lactose, glycine, sodium chloride, a pH buffering agent and a surfactant as additional ingredients for use in the treatment of a central nervous system disease.

The HGF preparation is preferably a lyophilized preparation (lyophilized HGF preparation) or an injection (HGF injection), and is more preferably an injection.

The HGF preparation, the lyophilized HGF preparation and the HGF injection, and their preferable embodiments and the like are as described above. In the treatment of a central nervous system disease, the HGF preparation is preferably administered intrathecally or intracerebroventricularly or administered into the spinal or cerebral parenchyma.

The present invention also includes a method for preventing the formation of HGF polymers (HGF protein-based polymers) in an aqueous solution containing an HGF protein, the method comprising adding lactose, glycine, sodium chloride, a pH buffering agent and a surfactant to the aqueous solution. In this method, the HGF protein, the lactose, the glycine, the sodium chloride, the pH buffering agent and the surfactant, and their preferable amounts and the like added to the aqueous solution are the same as described above for the HGF injection.

The present invention also includes a method for preventing the formation of HGF polymers (HGF protein-based polymers) in a lyophilized preparation containing an HGF protein, the method comprising adding lactose, glycine, sodium chloride, a pH buffering agent and a surfactant to the lyophilized preparation. In this method, the HGF protein, the lactose, the glycine, the sodium chloride, the pH buffering agent and the surfactant, and their preferable amounts and the like added to the lyophilized preparation are the same as described above for the lyophilized HGF preparation.

EXAMPLES

Hereinafter, the present invention will be illustrated in more detail by examples, but the present invention is not limited thereto.

Various kinds of additives were added to a recombinant human HGF protein (hereinafter referred to simply as HGF) consisting of the amino acid sequence represented by SEQ ID NO: 6, and the examination of stability and safety was conducted as below. In the following examples, the concentration "%" refers to a percent by mass unless otherwise specified. The HGF was prepared using CHO cells according to the method described in Biochem. Biophys. Res. Commun. 180: 1151-1158, 1991.

Example 1

Lactose and glycine were dissolved at the concentrations shown in Table 1 below in an HGF solution containing 5 mM citrate buffer (pH 6.0), 0.375 M sodium chloride and 0.005% polysorbate 80.

TABLE 1

| Ingredient | Concentration |
| --- | --- |
| HGF | 2.5 mg/mL |
| Lactose | 3.0 mg/mL |
| Glycine | 0.4 mg/mL |
| Trisodium citrate dihydrate/ citric acid hydrate | 5 mM (pH 6.0) |
| Sodium chloride | 0.375M |
| Polysorbate 80 | 0.005% |

The prepared solution was aseptically dispensed into 1-mL aliquots in vials (diameter 23×43 mm). The vials were half-plugged with rubber stoppers and aligned on a tray, and the tray was placed into a freeze dryer (Triomaster; manufactured by Kyowa Vacuum Engineering Co., Ltd). Preliminary freezing was performed at −50° C., followed by primary drying (−50° C.→−20° C./4 hours, −20° C./24 hours or longer, 0.01 to 0.1 Torr) and secondary drying (−20° C.→20 to 30° C./8 to 10 hours, 20 to 30° C./10 hours or longer, 0.01 to 0.1 Torr) to yield a lyophilized preparation. After the completion of freeze-drying, sterile nitrogen was fed into the drying chamber of Triomaster for pressure recovery (target pressure in the chamber: 88.0 kPa; primary pressure recovery). After the primary pressure recovery, the vials were fully plugged with the rubber stoppers, and the pressure in the chamber was returned to atmospheric pressure by sterile nitrogen supply (secondary pressure recovery). The vials were taken out of the chamber and immediately after that, sealed with caps. Thus, the lyophilized HGF preparation of the present invention was obtained.

Example 2

Another lyophilized HGF preparation was obtained in the same manner as described in Example 1 except that the concentration of the lactose was 7.5 mg/mL.

Example 3

Another lyophilized HGF preparation was obtained in the same manner as described in Example 1 except that the concentration of the lactose was 10 mg/mL.

Example 4

Lactose and glycine were dissolved at the concentrations shown in Table 2 below in an HGF solution containing 2 mM citrate buffer (pH 6.0), 0.15 M sodium chloride and 0.002% polysorbate 80, and thus an HGF injection was obtained. The HGF injection with the composition of Table 2 can also be obtained by another method, i.e., by dissolving the lyophilized HGF preparation obtained in Example 2 in 2.5 mL of distilled water for injection.

TABLE 2

| Ingredient | Concentration |
| --- | --- |
| HGF | 1.0 mg/mL |
| Lactose | 3.0 mg/mL |
| Glycine | 0.16 mg/mL |
| Trisodium citrate dihydrate/ citric acid hydrate | 2 mM (pH 6.0) |
| Sodium chloride | 0.15M |
| Polyscorbate 80 | 0.002% |

Experimental Example 1

To basic ingredients consisting of 10 mg/mL HGF, 10 mM citrate buffer (pH 6.0), 0.3 M sodium chloride and 0.03% polysorbate 80, the additives shown in Table 3 were added to prepare HGF solutions of formulations 1 to 3 (2 mL each). The HGF solutions were each freeze-dried in vials in the same manner as in Example 1 to give lyophilized preparations. Each lyophilized preparation was stored at 50° C. for one week for forced deterioration testing, and the polymer content was measured before and after the storage. The results are shown in Table 4.

TABLE 3

| Formulation No. | Additive | Basic ingredients |
| --- | --- | --- |
| 1 | — | 10 mg/mL HGF |
| 2 | 10 mg/mL purified sucrose | 10 mM citrate buffer (pH 6.0) |
| 3 | 10 mg/mL purified sucrose 5 mg/mL L-alanine | 0.3M sodium chloride 0.03% polysorbate 80 |

The polymer content of the HGF preparation was determined as follows. Each lyophilized preparation was dissolved in 2 mL of distilled water for injection and the resulting HGF solution was analyzed by high performance liquid chromatography (HPLC) under the conditions shown below. From the HPLC results, the area percentage (%) of the polymer (hereinafter referred to as polymer content (%)) was calculated by the following formula 1.

[Math. 1]

$$\text{Polymer content}(\%) = 100 \times A_A / (A_M + A_A) \quad \text{Formula 1}$$

In formula 1, $A_M$ stands for the HGF peak area and $A_A$ stands for the polymer peak area.

HPLC Conditions

Column: gel-filtration column (tradename: Superdex 200 10/300, manufactured by GE Healthcare)
Mobile phase: 58.44 g of sodium chloride, 2.94 g of trisodium citrate dihydrate and 0.1 g of polysorbate 80 were dissolved in purified water, and then purified water was further added to a total volume of 1 L. This solution was designated as solution A. 58.44 g of sodium chloride, 2.10 g of citric acid monohydrate and 0.1 g of polysorbate 80 were dissolved in purified water, and then purified water was further added to a total volume of 1 L. This solution was designated as solution B. Solution B was added to solution A and the pH of the mixed solution was adjusted to 6.0. The mixed solution was filtered through a 0.45-μm filter (trade name: Millicup-HV, pore size: 0.45 μm, manufactured by Merck) and degassed before use. The solution was stored at room temperature and used within two weeks.
Column temperature: 25° C.
Flow rate: 0.5 mL/min
Sample injection volume: 25 μL
Detection wavelength: 280 nm

TABLE 4

| Formulation No. | Polymer content (%) (mean, n = 3 each) | |
| --- | --- | --- |
| | Initial (before storage) | 50° C., 1-week storage |
| 1 | 0.84 | 6.12 |
| 2 | 0.58 | 1.29 |
| 3 | 0.56 | 0.90 |

For the lyophilized preparation produced from the HGF solution of formulation 1, which contained only the basic ingredients, the storage under severe conditions resulted in remarkable formation of HGF polymers. On the other hand, for the lyophilized preparations produced from the HGF solutions of formulations 2 and 3, polymer formation was prevented even under the severe conditions. These results demonstrate that purified sucrose or L-alanine has the effect of maintaining lyophilized HGF preparations in a stable condition, as is known so far.

Experimental Example 2

To basic ingredients consisting of 2.5 mg/mL HGF, 5 mM citrate buffer (pH 6.0), 0.375 M sodium chloride and 0.005% polysorbate 80, the additives shown in Table 5 were added to prepare HGF solutions of formulations 4 to 6 (1 mL each). The HGF solutions were each freeze-dried in vials in the same manner as in Example 1 to give lyophilized preparations. Each lyophilized preparation was stored at 50° C. for one week and the polymer content was measured before and after the storage in the same manner as in Experimental Example 1. The results are shown in Table 6.

TABLE 5

| Formulation No. | Additive | Basic ingredients |
|---|---|---|
| 4 | 0.4 mg/mL glycine | 2.5 mg/mL HGF |
| 5 | 0.4 mg/mL glycine | 5 mM citrate buffer (pH 6.0) |
|   | 7.5 mg/mL lactose | 0.375M sodium chloride |
| 6 | 0.4 mg/mL glycine | 0.005% polysorbate 80 |
|   | 20.0 mg/mL D-sorbitol |   |

TABLE 6

| | Polymer content (%) (mean, n = 3) | |
|---|---|---|
| Formulation No. | Initial (before storage) | 50° C. 1-week storage |
| 4 | 0.42 | 4.66 |
| 5 | 0.38 | 1.91 |
| 6 | 0.29 | 3.83 |

For the lyophilized HGF preparation of formulation 5, which contained glycine and lactose as additives, polymer formation was prevented, indicating high stability of the preparation.

Experimental Example 3

In this experimental example, the stability of lyophilized HGF preparations containing glycine and lactose as additives was examined. To basic ingredients consisting of 2.5 mg/mL HGF, 5 mM citrate buffer (pH 6.0), 0.375 M sodium chloride and 0.005% polysorbate 80, the additives shown in Table 7 were added to prepare HGF solutions of formulations 4, 5, 7 and 8 (1 mL each). The HGF solutions were each freeze-dried in vials in the same manner as in Example 1 to give lyophilized preparations. Each lyophilized preparation was stored at 25° C. for 1 or 2 months or at 50° C. for 2 weeks, and the polymer content was measured before and after the storage in the same manner as in Experimental Example 1. The results are shown in Table 8.

TABLE 7

| Formulation No. | Additive | Basic ingredients |
|---|---|---|
| 4 | 0.4 mg/mL glycine | 2.5 mg/mL HGF |
| 5 | 0.4 mg/mL glycine | 5 mM citrate buffer (pH 6.0) |
|   | 7.5 mg/mL lactose | 0.375M sodium chloride |
| 7 | 0.4 mg/mL glycine | 0.005% polysorbate 80 |
|   | 10 mg/mL lactose |   |
| 8 | 0.4 mg/mL glycine |   |
|   | 10 mg/mL purified sucrose |   |

TABLE 8

| | Polymer content (%) (mean, n = 3) | | | |
|---|---|---|---|---|
| Formulation No. | Initial (before storage) | 25° C., 1-month storage | 25° C., 2-month storage | 50° C., 2-week storage |
| 4 | 0.91 | 1.81 | 1.91 | 5.63 |
| 5 | 0.45 | 0.63 | 0.86 | 1.37 |
| 7 | 0.50 | 0.69 | 0.75 | 1.29 |
| 8 | 0.49 | 0.67 | 0.75 | 0.97 |

For the lyophilized preparations produced from the HGF solutions of formulations 5 and 7, which contained glycine and lactose as additives, increase in the polymer content was only slight even after 2 months of storage at room temperature (25° C.). Moreover, even after the storage under severe conditions, i.e., at 50° C. for 2 weeks, the polymer content was as low as only slightly more than 1%, indicating that polymer formation was prevented. The effect of preventing polymer formation in the lyophilized preparations produced from the HGF solutions of formulations 5 and 7 was almost comparable to that in formulation 8, in which the additive other than glycine was purified sucrose, which is known to be effective for the stabilization of lyophilized HGF preparations.

Experimental Example 4

The lyophilized HGF preparation obtained in Example 2 was dissolved in 2.5 mL of distilled water for injection to give an HGF injection with the composition of Table 2. The injection was stored at 40° C. for 2 weeks in an airtight container. The polymer content of the HGF injection was measured before and after the storage in the same manner as in Experimental Example 1. The biological activities of HGF in the HGF injection before and after the storage were evaluated using the growth of the mink lung epithelial cell line MvlLu (Riken, BRC ID: RCB0996) as an indicator.

The polymer contents in the HGF injection before and after storage were 1.54% and 2.67%, respectively. That is, the increase in the polymer content during 2 weeks of storage at 40° C. was only about 1%. The biological activity of HGF in the HGF injection after 2 weeks of storage at 40° C. was 89.4% (relative value calculated on the assumption that the activity before the storage was 100%) of that before the storage and was maintained at a high level. These results show that the HGF injection of the present invention was kept almost stable during 2 weeks of storage at 40° C.

Test Example 1

Forty-five microliters of a test sample shown in Table 9, i.e., HGF solution 1 or 2, vehicle (vehicle A or B) or physiological saline, was intrathecally administered as a single bolus to rats for examination of the safety for the central nervous system. On the ground that the volume of spinal fluid in a rat is only about 200 μL, if an excessive volume of a solution is administered thereinto as a single bolus, the bolus administration itself may induce abnormalities in rats. Therefore, the maximum permissible volume per rat for single bolus intrathecal administration was set at 45 μL.

The skin in the area of the neck and the back of each rat was shaved with an electric hair clipper under pentobarbital anesthesia. The shaved area was cleaned and disinfected with ethanol for disinfection and ISODINE solution 10% (trade name, Meiji, Co., Ltd.: 10% povidone iodine solution). An incision was made through the back skin to expose the vertebral section from the 11th thoracic vertebra to the 2nd lumbar vertebra. The ligament between the 12th and 13th thoracic vertebrae was excised to expose the dura mater. A small incision was made through the exposed dura mater and the arachnoid mater, and the outflow of spinal fluid was confirmed. Immediately after that, the tip of a polyurethane catheter (a two-piece catheter prepared by connecting MRE025 (OD: 0.25 mm, 10 cm) and MRE010 (OD: 0.65 mm, 2.5 cm); Braintree, USA) filled with physiological saline (Otsuka Pharmaceutical Factory) was inserted about 2.5 cm from the incision into the intrathecal space (toward the head). The catheter was fixed to peripheral tissues with medical Aron Alpha (trade name: Aron Alpha A "Sankyo", DAIICHI SANKYO Company, Limited). In addition, the open end of the catheter was closed by heat sealing, and the outer end of the catheter was exposed with an appropriate length on the cervical skin surface. The incision was closed with a suture. Each rat was kept warm on a heating pad until emergence from anesthesia, and then returned to a breeding cage. On the day following the catheter placement, 45 μL of the test sample shown in Table 9, i.e., HGF solution 1 or 2, vehicle (vehicle A or B) or physiological saline, was administered as a single bolus through the retained catheter to the rats in an awake state. Subsequently, 10 μL of physiological saline was injected through the retained catheter (for the purpose that the HGF solution or the vehicle which remained in the catheter was pushed into the intrathecal space). The catheter tip was then closed by heat sealing and placed under the skin, and the conditions of the rats were observed.

TABLE 9

| Test sample | Composition | Administration volume | Number of animals | Observation of rats |
|---|---|---|---|---|
| Physiological saline | | 45 μL | 3 | No rats showed any abnormalities. |
| Vehicle A | 10 mM citrate buffer (pH 6.0) 0.3M sodium chloride 0.05% polysorbate 80 10 mg/mL purified sucrose 5 mg/mL L-alanine | 45 μL | 3 | All rats showed reduced locomotor activity, salivation, convulsions, etc immediately after administration, but returned to normal 1 hour after administration. |
| Vehicle B | 2 mM citrate buffer (pH 6.0) 0.15M sodium chloride 0.002% polysorbate 80 0.16 mg/mL glycine 3 mg/mL lactose | 45 μL | 6 | No rats showed any abnormalities. |
| HGF solution 1 | 1 mg/mL HGF 2 mM citrate buffer (pH 6.0) 0.15M sodium chloride 0.002% polysorbate 80 0.16 mg/mL glycine 3 mg/mL lactose | 45 μL | 3 | No rats showed any abnormalities. |
| HGF solution 2 | 1 mg/mL HGF 2 mM citrate buffer (pH 6.0) 0.15M sodium chloride 0.002% polysorbate 80 0.16 mg/mL glycine 4 mg/mL purified sucrose | 45 μL | 3 | All rats showed abnormal phonation, limb rigidity, etc. immediately after administration, but returned to normal 20 minutes after administration. |

The bolus intrathecal administration of physiological saline to the rats did not cause abnormalities. On the other hand, in the case of the intrathecal administration of vehicle A, which was prepared by blending additives known to have a stabilizing effect on HGF preparations, neurological abnormalities such as reduced locomotor activity, salivation and convulsions were found in the rats, albeit transiently. In contrast, the intrathecal administration of vehicle B, which was prepared by blending the additives used in the HGF preparation of the present invention, did not cause abnormalities in the rats as in the case of the administration of physiological saline. Vehicle B was used for the preparation of HGF solution 1 (this solution was exactly the same as the injection of Example 4 and corresponds to an embodiment of the HGF injection of the present invention), and the intrathecal administration of HGF solution 1 did not cause abnormalities in the rats, either. These results demonstrate that the HGF injection of the present invention does not have adverse effects on the central nervous system and therefore its composition is very safe. On the other hand, in the case of the intrathecal administration of HGF solution 2, which was prepared with a vehicle having the same composition as that of vehicle B except for containing sucrose instead of lactose, neurologically abnormal conditions such as abnormal phonation and limb rigidity were observed in the rats for about 20 minutes after the administration.

Test Example 2

A rat spinal-cord-injury model was prepared, and from immediately after the onset of the injury, repetitive intrathecal administration of an HGF solution was started (45 μL/shot, 3 times/week, for 4 weeks) (HGF administration group; n=6). The HGF solution used was the same as the HGF solution with the composition of Table 2, and was obtained by redissolving the lyophilized preparation of Example 2 in 2.5 mL of distilled water for injection. For the control group, a vehicle (2 mM citrate buffer (pH 6.0), 0.15 M sodium chloride, 0.002% polysorbate 80, 0.16 mg/mL glycine and 3 mg/mL lactose), which did not contain HGF, was similarly administered to spinal-cord-injury model rats (n=6).

The spinal-cord-injury model rats were prepared as follows. The skin in the area of the neck down to the waist of each rat was shaved with an electric hair clipper under ketamine and xylazine anesthesia. The shaved area was cleaned with 70% alcohol and ISODINE solution 10% (trade name, Meiji, Co., Ltd.: 10% povidone iodine solution). An incision was made through the back skin to expose the vertebral section from the 6th thoracic vertebra to near the 5th lumbar vertebra. The vertebral arches at the 9th and 10th thoracic vertebrae and the ligament therebetween were excised to expose the dura mater. Immediately after that, a 10-g weight was dropped from a height of 25 mm onto the exposed dura mater at the 10th thoracic level using MASCIS Impactor (Rutgers University, USA) to induce spinal cord injury. Immediately after the onset of spinal cord injury, the ligament between the 1st and 2nd lumbar vertebrae was excised to expose the dura mater, and a small incision was made through the dura mater and the arachnoid mater. The leakage of spinal fluid was confirmed, and immediately after that, the tip of a polyurethane catheter (a two-piece catheter prepared by connecting MRE025 (OD: 0.25 mm, 10 cm, Braintree, USA) and MRE010 (OD: 0.65 mm, 2.5 cm, Braintree, USA)) was inserted into the intrathecal space (toward the head) until it reached the neighborhood of the site of spinal cord injury. The catheter was fixed to muscle layers with medical Aron Alpha (trade name: Aron Alpha A "Sankyo", manufactured by DAIICHI SANKYO Company, Limited) and retained. After the first shot of the test solution (HGF solution or vehicle), the outer end of the catheter was exposed with an appropriate length on the cervical skin surface, and the incision was closed with a suture. Each animal was kept warm on a heating pad until emergence from anesthesia, and then returned to a breeding cage. From then on, the HGF solution or the vehicle was repeatedly administered through the retained catheter 3 times/week for 4 weeks. At every administration, injection of 45 μL of the HGF solution or the vehicle was followed by injection of 10 μL of physiological saline (for the purpose that the HGF solution or the vehicle which remained in the catheter was pushed into the intrathecal space). After every administration, the open end of the catheter was closed by heat sealing.

The hindlimb motor function of the rats was evaluated over time using the BBB scale (highest score of 21: a 21-point rating scale of 0 (complete paralysis) to 21 (normal hindlimb movement)) (Basso D M, Beattie M S, Bresnahan J C: A sensitive and reliable locomotor rating scale for open field testing in rats. J Neurotrauma 12: 1-21, 1995) to examine the therapeutic effect of HGF on spinal cord injury. The BBB score was zero in all the animals on the day following the onset of spinal cord injury. After 4 weeks from the onset of spinal cord injury, however, the mean of the BBB score in the HGF administration group was recovered to 10 or more, which was significantly higher than the score (mean: less than 10) in the vehicle administration group (control group). These results show that HGF has a therapeutic effect on spinal cord injury. During the entire 4-week administration period, no abnormal conditions except for spinal cord injury were observed either in the rats of the vehicle administration group (control group) or in the rats of the HGF administration group. The autopsy of the rats after 4 weeks from the onset of spinal cord injury also showed no abnormalities in the spinal cord except for the site of spinal cord injury. As shown by these results, the HGF solution prepared by redissolving the lyophilized preparation of Example 2 was safe and effective for the treatment of spinal cord injury.

INDUSTRIAL APPLICABILITY

According to the present invention, an HGF preparation which is excellent in storage stability for pharmaceutical use is provided. The HGF injection of the present invention can be administered intrathecally or intracerebroventricularly or administered into the spinal or cerebral parenchyma for the treatment of various central nervous system diseases such as ALS and spinal cord injury. Therefore, the present invention is useful in the medical field etc.

The invention claimed is:

1. A method of treating a central nervous system disease, which comprises a step of administering to a patient with the central nervous system disease an injection composition comprising a hepatocyte growth factor (HGF) protein as an active ingredient to treat the central nervous system disease wherein neuronal cell survival and/or neurite outgrowth is promoted,
   wherein the injected composition is selected from the group consisting of (1) or (2),
   (1) an aqueous solution containing the HGF protein and lactose, glycine, sodium chloride, a pH buffering agent and a surfactant, wherein the content of the lactose is in the range of 1 to 5 parts by weight relative to 1 part by weight of the HGF protein, and wherein the concentration of the glycine in the aqueous solution is in the range of 0.1 to 10 mg/mL, or
   (2) a re-dissolution liquid prepared by dissolving the HGF preparation which is obtained by freeze-drying of an aqueous solution comprising an HGF protein and lactose, glycine, sodium chloride, a pH buffering agent and a surfactant, wherein the content of the lactose is in the range of 1 to 5 parts by weight relative to 1 part by weight of HGF protein, and wherein the concentration of the glycine in the aqueous solution is in the range of 0.1 to 10 mg/mL, in a pharmaceutically acceptable solvent,
   wherein the central nervous system disease is amyotrophic lateral sclerosis (ALS), Alzheimer's disease, Parkinson's disease, Huntington's disease, spinocerebellar ataxia, spinal cord injury, cerebral infarction, cerebral ischemia or multiple sclerosis,
   wherein the daily dose of the HGF protein is 0.01 to 50 mg.

2. The method according to claim 1, wherein the injection is administered intrathecally or intracerebroventricularly or administered into spinal or cerebral parenchyma of the patient.

3. The method according to claim 1, wherein the concentration of the lactose in the aqueous solution is in the range of 0.1 to 100 mg/mL.

4. The method according to claim 1, wherein the concentration of the HGF protein in the aqueous solution is in the range of 0.1 to 20 mg/mL.

5. The method according to claim 1, wherein the pH buffering agent is a combination of citric acid or a hydrate thereof with a salt of citric acid.

6. The method according to claim 1, wherein the surfactant is polysorbate.

7. The method according to claim 1, wherein the HGF protein is a human HGF protein.

8. The method according to claim 1, wherein the HGF protein is a protein consisting of an amino acid sequence represented by SEQ ID NO: 5 or SEQ ID NO: 6.

9. The method according to claim 1, wherein the HGF protein is a protein which has 80% or more sequence identity with an amino acid sequence represented by SEQ ID NO: 5 and has a biological activity of HGF.

* * * * *